United States Patent [19]

Fickenscher

[11] Patent Number: 5,292,664
[45] Date of Patent: Mar. 8, 1994

[54] FUNCTIONAL TEST AND REAGENT FOR DETERMINING FIBRINOGEN

[75] Inventor: Karl Fickenscher, Marburg, Fed. Rep. of Germany

[73] Assignee: Behringwerke Aktiengesellschaft, Marburg, Fed. Rep. of Germany

[21] Appl. No.: 958,770

[22] Filed: Oct. 9, 1992

[30] Foreign Application Priority Data

Oct. 14, 1991 [DE] Fed. Rep. of Germany ....... 4133946

[51] Int. Cl.$^5$ .................. G01N 33/86; C12Q 1/56
[52] U.S. Cl. .................................. 436/69; 436/34; 436/63; 436/86; 435/13; 435/23
[58] Field of Search .............. 436/34, 69, 86, 87, 436/63, 164; 435/13, 23

[56] References Cited

U.S. PATENT DOCUMENTS

| | | | |
|---|---|---|---|
| 4,210,420 | 7/1980 | Baughman et al. | 436/69 |
| 4,455,290 | 1/1984 | Oleva et al. | 424/1.1 |
| 4,692,406 | 9/1987 | Becker | 436/69 X |
| 5,093,237 | 3/1992 | Enomoto | 436/69 X |
| 5,156,974 | 10/1992 | Grossman et al. | 436/69 |
| 5,197,017 | 3/1993 | Carroll et al. | 436/69 X |

FOREIGN PATENT DOCUMENTS

| | | |
|---|---|---|
| 1137269 | 4/1985 | European Pat. Off. |
| 3811647A1 | 10/1989 | Fed. Rep. of Germany |
| 4014655A1 | 11/1991 | Fed. Rep. of Germany |
| 0053848 | 3/1985 | Japan ............... 436/69 |

OTHER PUBLICATIONS

Gerinnungsphysiologische Schnellmethode Zur Bestimmung Des Fibrinogens, A. Clauss, Acta Haemat, 17:237-246 (1957).
Fibrinogen as a Major Risk Factor in Cardiovascular Disease, Cook et al., TIPS, 11:444-451 (1990).
Fibrinogen Level as a Predictor of Mortality in Survivors of Myocardial Infarction, Cooper et al., Fibrinolysis, 5:105-108 (1991).
Optimized Microturbidimetric Assay for Fibrinogen, Macart et al., Clin. Chem., 35(2):211-214 (1989).
A Rapid Enzymatic Method For Assay Of Fibrinogen Fibrin Polymerization Time (FPT Test), Vermylen et al., Clinica Chimica Acta, 8:418-424 (1963).
A New Method For The Determination Of Fibrinogen In Small Samples Of Plasma Ratnoff et al., J. Lab. Clin. Med., 37:316-320 (1951).
Faster Determination of Clottable Fibrinogen in Human Plasma: An Improved Method and Kinetic Study, Inada et al., Clinical Chemistry, 24(2):351-353 (1978).
Kinetic Determination Of Fibrinogen With a Centrifugal Analyzer, E. Denegri et al., Clinical Chemistry, 28(7):1502-1505 (1982).
Synthetic Peptide Dericatives That Bind to Fibrinogen And Prevent The Polymerization of Fibrin Monomers, Laudano et al., Proc. Natl. Acad. Sci. USA, 75(7):3085-3089 (1978).
Measurement of Blood Coagulation Factor XIIIa Formation in Plasma Containing Glycyl-L-Prolyl-L-Arginyl-L-Proline, Miraglia et al., Anal. Biochem. 144:165-171 (1985).

*Primary Examiner*—James C. Housel
*Assistant Examiner*—Milton I. Cano
*Attorney, Agent, or Firm*—Finnegan, Henderson, Farabow, Garrett & Dunner

[57] ABSTRACT

A method and reagent for determining fibrinogen from undiluted plasma samples. The use of undiluted plasma as sample is made possible by the use of a specific peptide inhibitor of fibrin aggregation in a concentration which permits aggregation of fibrin but with reduced speed, so that coagulation time can be measured easily. The range of fibrinogen concentrations which can be measured is increased as compared to that of known methods, and the measurement can be fully automated without prediluting the sample. A biological fluid, e.g., undiluted plasma, is incubated with a reagent containing at least one inhibitor of fibrin aggregation in an amount effective to increase coagulation time to allow measurement of the fibrin concentration, e.g., a coagulation time of about 50 to 150 seconds at a fibrin concentration of 1 gram/liter, and thrombin, or a protease of analogous activity in an amount, which immediately converts all the fibrinogen into soluble fibrin, e.g., in an excess of at least 20 U per ml of plasma. The coagulation time is then determined.

5 Claims, 1 Drawing Sheet

FUNCTIONAL TEST AND REAGENT FOR DETERMINING FIBRINOGEN

The invention relates to a method and to a reagent for determining fibrinogen from undiluted plasma samples.

Fibrinogen is a glycoprotein with a molecular weight of 340,000. Proteolytic elimination of fibrinopeptide A and B by thrombin results in the formation of fibrin monomers which aggregate to give fibrin. This last step in the coagulation of blood is essential because it represents the formation of the clot. The concentration of fibrinogen is very variable. It may decrease due to consumption (acquired fibrinogen deficiency), but it may also be greatly increased in the acute phase of a disorder, for example after burns. Because of its important function for plasmatic coagulation, fibrinogen is the protein which is determined most often in coagulation diagnosis. Recent investigations show that chronically increased concentrations of fibrinogen correlate with an increased probability of cardiovascular disorders (Cook, N. S. & Ubben D. 1990, TIPS 11: 444–451; Cooper J. & Douglas A. S. 1991, Fibrinolysis 5: 105–108).

A number of methods for determination of fibrinogen are known.

Various methods for immunological determinations are known but do not allow conclusions to be drawn about the functioning ability of the molecules found. They are unable to distinguish between fibrinogen, fibrin and fibrin(ogen) degradation products and therefore provide only limited information for the physician and are not the subject of the invention.

Methods which utilize precipitation reactions with various reagents are likewise known (Macart, M. et al. 1989, Clin. Chem. 35: 211-214). Since no clot is generated by thrombin in these cases, it is likewise impossible to determine the functional activity. In addition, the precipitation reactions are very nonspecific so that other proteins are also included and may therefore falsify the result. These methods have not come to be used in routine diagnosis and are likewise not the subject of the invention.

The methods for determining fibrinogen which is capable of functioning can be divided into two essential groups:

1. Methods in which the coagulation time of a diluted plasma is determined. This time depends on the fibrinogen content of the sample. The sample to be determined must therefore be previously diluted to an extent such that measurable coagulation times are achieved (Clauss, A. 1957, Acta Haemat., 17: 237-246; Vermylen C. et al. 1963, Clin. Chim. Acta 8: 418–424). In this method increasing amounts of fibrinogen correlate with decreasing coagulation time.
2. Methods in which the amount of clot produced is measured. This can take place, for example, by the clot being isolated from the test mixture and washed, and the amount of protein contained therein being determined (Ratnoff, O. D. and Menzie, C. A. B., 1951, J. Lab. Clin. Med. 37:316-320). This method is very labor-intensive and time-consuming and is therefore not carried out in routine diagnosis.

Optical systems are frequently used to measure the overall rise reached in the optical density or the light scattering on onset of coagulation (Inada Y. et al. 1978, Clin. Chem. 24: 351-353; Denegri E. & Prencipe L. 1982, Clin. Chem. 28: 1502-1505.

Related to the latter method is a method which employs for the reaction of fibrinogen a thrombin-like snake venom enzyme from members of the genus Agkistrodon (EP 0 137 269). A photometric system is required for the evaluation, because the aggregation rate must be determined. The rate of rise in turbidity is a measure of the fibrinogen concentration, similar to the abovementioned methods in which the total rise in the signal is employed for the evaluation. It is additionally possible in this case to use the time of the rise in turbidity as the measure of fibrinogen degradation products.

It is particularly disadvantageous with the method according to the state of the art (Clauss, A. (1957)) detailed under 1. that the samples must previously be diluted about 1:10 in an additional step. If undiluted samples are employed, the necessarily high concentrations of thrombin result in extremely short coagulation times which can no longer be evaluated. When the fibrinogen concentrations are very high in fact a second dilution step and a repeat measurement are often also necessary.

If the preliminary dilution were to be omitted in this method, and the amount of thrombin were to be reduced to avoid coagulation times which are too short to be useful, increases in the coagulation time both at low and at increased fibrinogen concentration are measured so that the measured coagulation time can no longer be assigned to one concentration.

Another disadvantage of the method according to the state of the art is that, because of the high dilution, only a very weak and small clot can be produced. Although mechanically measuring instruments are able to detect this, their precision is poor compared with coagulation tests in which undiluted plasma is employed. The photometric instruments which are increasingly employed now are very often no longer able reliably to detect the weak clots. This is why these instruments are frequently used with other methods which are intrinsically less favorable and provide less information.

Methods which process a clot in order to detect the amount of fibrinogen present are too labor-intensive and thus not suitable for routine use.

Turbidimetric or nephelometric methods depend on the intrinsic turbidity of the samples and therefore do not always provide reliable results; they are confined to instruments specifically set up for them, which limits their general utilisability.

The invention was based on the object of finding a method which makes it possible to determine fibrinogen with the intruments customary in the routine coagulation laboratory without the need to pretreat the sample.

It has been found, surprisingly, that this can be achieved by partially inhibiting the aggregation of the fibrin by a specific inhibitor. The coagulation of the fibrin intrinsically means the same as the aggregation of the fibrin monomers, but it is possible by suitable choice of the inhibitor concentration to adjust the coagulation time so that samples both of very high and of very low concentration coagulate within a time frame permitting practicable measurement. A further achievement was that the difference in the coagulation time between two given fibrinogen concentrations has become distinctly larger than in the state of the art. The resulting greater spread in the reference plot makes an essential contribution to precise determination of fibrinogen.

In the method according to the invention, a large excess of thrombin or a protease with analogous activity such as batroxobin (a protease from the venom of the snake Agkistrodon rhodostoma) is employed so that all the fibrinogen is immediately converted into soluble fibrin. This means that the coagulation time now depends only on the fibrin aggregation rate. At a constant concentration of the inhibitor, this is a function of the fibrin concentration.

DETAILED DESCRIPTION OF THE INVENTION

Figure 1:
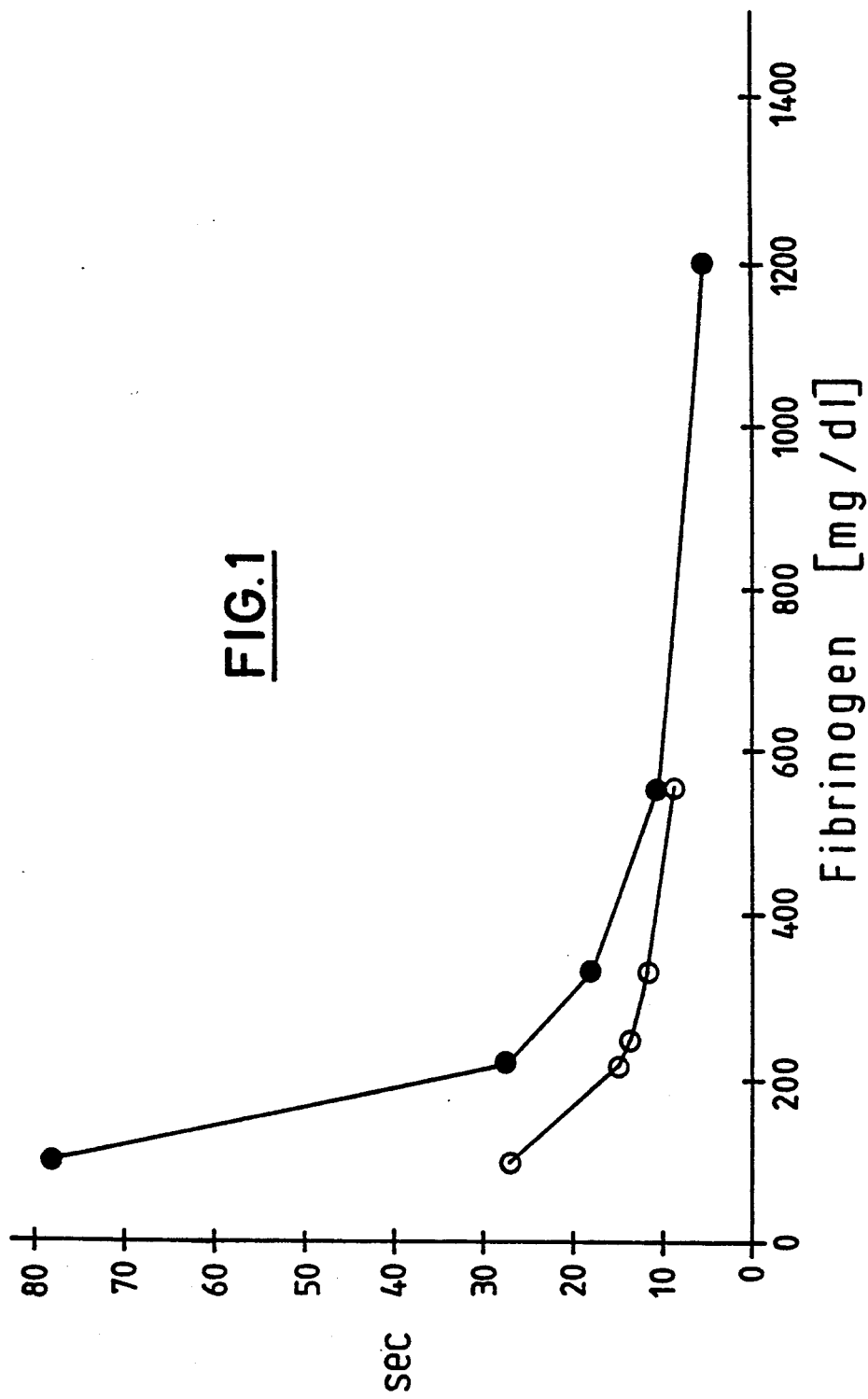
FIG. 1 is a graph representing coagulation time as a function of the fibrinogen concentration of a plasma sample.

Suitable inhibitors are peptides which have a structure analogous to the amino-terminal end of the human fibrin α-chain. These peptides, as well as the inhibition of fibrin aggregation achievable therewith, are known per se (Laudano A. P. et al. Proc. Natl. Acad. Sci. USA (1978), 3085-3089; DE 40 14 655).

Inhibitors of this type have also come to be used in various coagulation test systems in which complete inhibition of clot formation is necessary (Miragla C. C. et al. Anal. Biochem. (1985), 144, 165-171, DE 38 11 647). They are always employed in a large excess in order to avoid interference with the actual test which is independent of the clot inhibitor itself.

The concentration in the method according to the invention is adjusted so that the coagulation time allows practicable measurement of the fibrin concentration, and the coagulation time ought preferably to be about 50 to 150 s at a fibrin concentration of 1 g/l.

The method according to the invention is preferably carried out in the presence of a water-soluble polyalcohol, for example polyethylene glycol 6000. The effect of this is that even low fibrin concentrations still aggregate and are thus measurable. It is furthermore preferable to carry out the method in the presence of a heparin inhibitor such as, for example, Polybrene (hexadimethrine bromide), or protamine sulfate or chloride. This makes it possible to prevent the AT III present in heparinized samples inhibiting, in conjunction with the heparin, the thrombin present in the reagent and thus adversely affecting the test.

The peptides described in DE 40 14 655 are preferably used as inhibitor of fibrin aggregation.

The invention thus relates to a method for determining fibrinogen, wherein the sample is employed undiluted, and an inhibitor of fibrin aggregation is employed.

The invention furthermore relates to a method as described above wherein the coagulation time is measured.

The invention additionally relates to a method as described above wherein the coagulation is induced by addition of thrombin or of a protease with analogous activity.

The invention furthermore relates to a method as described above wherein when thrombin is used it is added in an excess of at least 20 U per ml of plasma.

The invention additionally relates to a method as described above wherein sample and reagent are mixed in a ratio of from 1:1 to 1:5.

The invention furthermore relates to a method as described above wherein only one reagent is employed.

The invention additionally relates to a reagent which preferably contains 10-600 U/ml thrombin, 20-2000 μg/ml of the aggregation inhibitor, 0.02-0.8% of a water-soluble polyalcohol, 50 to 250 mM sodium chloride, 20-100 mM of a buffer, pH 7.0 to 8.5, 2 to 25 mM calcium chloride, 2 to 100 μg/ml of a heparin-neutralizing substance and bulking agents.

Examples of bulking agents are sugars, sugar alcohols, amino acids, hydrated collagen or albumin (such as, for example, sucrose, mannitol, glycine, polygeline).

A particularly preferred reagent contains 30-300 U/ml thrombin, 100-500 μg/ml of an aggregation inhibitor with the amino-acid sequence G-P-R-P-A-amide, 0.06-0.1% polyethylene glycol 6000, 100 to 150 mM NaCl, 50 mM Tris pH 7.8-8.3, 10 mM $CaCl_2$, 10-20 μg/ml polybrene and 1% bovine serum albumin.

A typical procedure for the method according to the invention may be as follows:

1 to 5 times, preferably twice, the volume of the reagent according to the invention is added to a sample, for example citrated plasma, which is equilibrated at, preferably, 37° C.

The coagulation time is determined by measurement methods known per se.

The following examples are intended to explain the invention in detail:

EXAMPLE 1

Preparation of a suitable reagent

The following substances are dissolved in the stated concentration in water, and the pH is adjusted. The solution is then ready for use.

200 μg/ml aggregation inhibitor (G-P-R-P-A-amide), 50 U/ml bovine thrombin, 0.08% polyethylene glycol 6000, 110 mM NaCl, 15 μg/ml Polybrene, 1% bovine serum albumin, 10 mM $CaCl_2$, 50 mM Tris, pH 8.0.

EXAMPLE 2:

Procedure for a fibrinogen determination in various instruments

100 μl of citrated plasma were equilibrated at 37° C., and 200 μl of reagent according to Example 1 (37° C.) were added.

Table 1 shows the coagulation times determined in instruments with various methods for detecting the time of coagulation.

Table 1

Coagulation times for samples with different fibrinogen concentrations on measurement in various instruments. The instruments were: (A) Schnitger and Gross coagulometer (electromechanical, supplied by Amelung); (B) Fibrintimer (turbodensitometric, supplied by Labor); (C) Chromotimer (photometric, supplied by Behring); (D) Biomatic 4000 (vibration damping, supplied by Sarstedt).

| Fibrinogen | Coagulation times in sec | | | |
|---|---|---|---|---|
| g/l | A | B | C | D |
| 12 | 8.0 | 8.7 | 7.9 | 7.8 |
| 5 | 13.5 | 14.6 | 14.0 | 14.9 |
| 3.5 | 20.3 | 19.6 | 20.7 | 19.7 |
| 2.5 | 26.9 | 24.0 | 28.9 | 23.9 |
| 1.0 | 86.9 | 68.4 | 90.4 | 68.8 |
| 0.8 | 117.3 | 93.0 | 196.6 | 92.9 |
| 0.6 | 174.4 | 151.3 | — | 152.5 |

EXAMPLE 3

Comparison of the reference plot according to the method according to the invention and to the method according to the state of the art with preliminary dilution of sample Samples with different fibrinogen concentrations were measured in an instrument (Fibrintimer 2-channel, Behring-Werke) using the method according to the invention and using a commercially available test (Multifibren ®, Behringwerke). In the commercially obtainable method, the plasma sample undergoes preliminary 1:10 dilution with buffer. 200 µl of the diluted sample are incubated for 1 min and then 100 µl of the reagent are added and the coagulation time is determined. FIG. 1 shows the coagulation times obtained with the two methods as a function of the fibrinogen concentration in the sample.   method according to the state of the art;   method according to the invention. It is not possible with the method customary hitherto to measure samples in the particularly high region and therefore data points are missing.

I claim:

1. A method for the determination of fibrinogen in an undiluted sample of a biological fluid, comprising the steps of:
   a) incubating the undiluted sample with a reagent wherein said sample and reagent are mixed in a ratio of from 1:1 to 1:5, the reagent comprising at least one inhibitor of fibrin aggregation to increase coagulation time to about 50 to 150 seconds; and thrombin or a protease with analogous activity in an amount effective to convert fibrinogen into soluble fibrin without the inhibition of fibrin aggregation;
   b) determining the coagulation time; and
   c) correlating fibrinogen with coagulation time.

2. The method as claimed in claim 1, wherein the amount of thrombin or protease in the reagent is an amount effective to yield a coagulation time of less than 10 seconds without inhibition of fibrin aggregation.

3. The method as claimed in claim 1, wherein when thrombin is used it is added in an excess of at least 20 U per ml of plasma.

4. The method as claimed in claim 1, wherein only one reagent is employed.

5. The method as claimed in claim 1, wherein a reagent which contains 10–200 U/ml thrombin, 0.02–0.8% of a water-soluble polyalcohol, 50 to 250 mM sodium chloride, 20–100 mM of a buffer of pH 7.0 to 8.5, 2 to 25 mM calcium chloride, 2 to 100 µg/ml of a heparin neutralizer, 20–1000 µg/ml of a peptide which inhibits fibrin aggregation, and bulking agents, is employed.

* * * * *